(12) United States Patent
Richard

(10) Patent No.: US 8,992,993 B2
(45) Date of Patent: *Mar. 31, 2015

(54) CROSS-LINKED POLYMER PARTICLES

(71) Applicant: Boston Scientific Scimed, Inc., Maple Grove, MN (US)

(72) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,488

(22) Filed: Apr. 8, 2013

(65) Prior Publication Data

US 2013/0224487 A1    Aug. 29, 2013

Related U.S. Application Data

(63) Continuation of application No. 11/856,237, filed on Sep. 17, 2007, now Pat. No. 8,414,927.

(60) Provisional application No. 60/856,662, filed on Nov. 3, 2006.

(51) Int. Cl.

| | | |
|---|---|---|
| *A61K 9/14* | (2006.01) | |
| *A61K 9/50* | (2006.01) | |
| *A61K 31/4192* | (2006.01) | |
| *B32B 5/16* | (2006.01) | |
| *A61K 9/00* | (2006.01) | |
| *A61K 9/16* | (2006.01) | |
| *C08J 3/24* | (2006.01) | |
| *C08J 9/36* | (2006.01) | |

(52) U.S. Cl.

CPC ............... *B32B 5/16* (2013.01); *A61K 31/4192* (2013.01); *A61K 9/0019* (2013.01); *A61K 9/0034* (2013.01); *A61K 9/167* (2013.01); *A61K 9/1676* (2013.01); *A61K 9/5031* (2013.01); *A61K 9/5036* (2013.01); *A61K 9/5057* (2013.01); *A61K 9/5073* (2013.01); *A61K 9/5078* (2013.01); *C08J 3/24* (2013.01); *C08J 9/365* (2013.01); *C08J 2201/024* (2013.01); *C08J 2329/04* (2013.01)

USPC ............. 424/501; 424/430; 424/489; 514/93; 514/772.2

(58) Field of Classification Search
None
See application file for complete search history.

(56) References Cited

U.S. PATENT DOCUMENTS

| | | | | |
|---|---|---|---|---|
| 5,429,826 | A  * | 7/1995 | Nair et al. | 424/501 |
| 8,414,927 | B2 * | 4/2013 | Richard | 424/501 |
| 2006/0240092 | A1 * | 10/2006 | Breitenkamp et al. | 424/450 |

OTHER PUBLICATIONS

MJ Joralemon, RK O'Reilly, CJ Hawker, KL Wooley. "Shell Click-Crosslinked (SCC) Nanoparticles: A New Methodology for Synthesis and Orthogonal Functionalization." Journal of the American Chemical Society, vol. 127, 2005, pp. 16892-16899.*

United States Patent Office, Patent Trial and Appeal Board. Appeal 2011-005836 (U.S. Appl. No. 11/856,237). 11 total pages. (cover page and pp. 1-10), Sep. 27, 2012.*

* cited by examiner

*Primary Examiner* — Frederick Krass
*Assistant Examiner* — Isaac Shomer
(74) *Attorney, Agent, or Firm* — Kacvinsky Daisak Bluni PLLC

(57) ABSTRACT

Biodegradable cross-linked particles, as well as related compositions and methods, are disclosed.

7 Claims, 6 Drawing Sheets

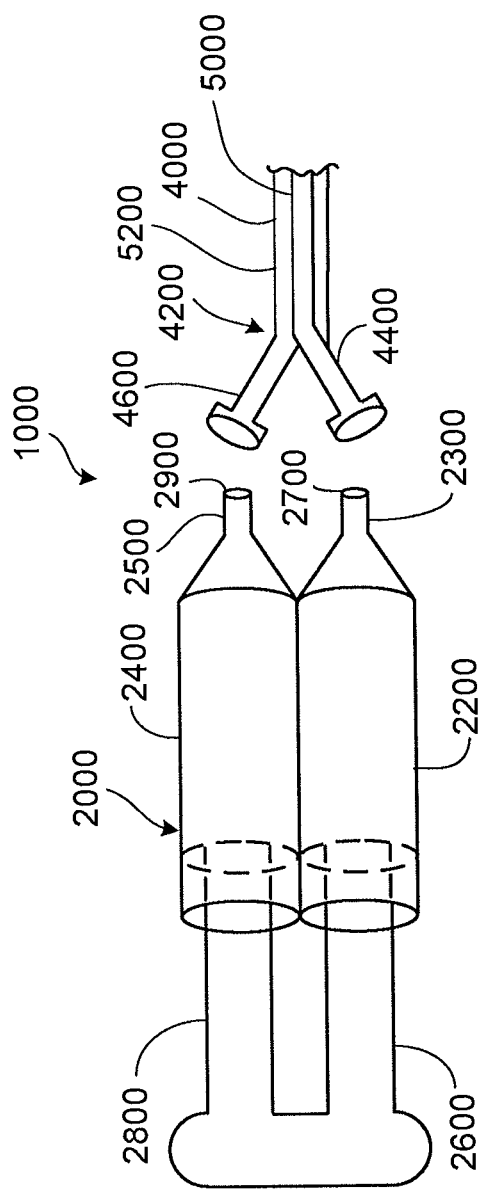
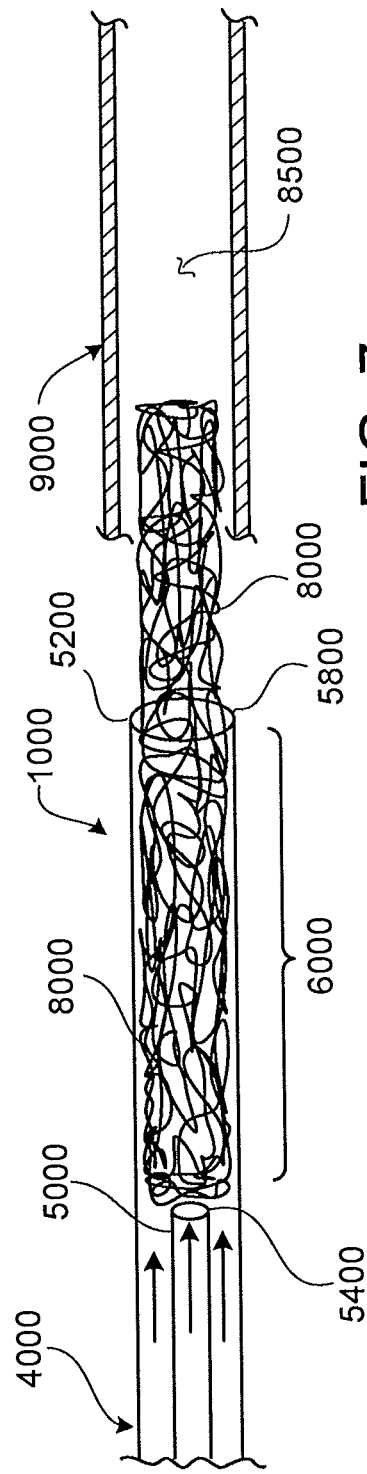
FIG. 6
FIG. 7

CROSS-LINKED POLYMER PARTICLES

CROSS-REFERENCE TO RELATED APPLICATION

This application is a continuation of U.S. application Ser. No. 11/856,237, filed Sep. 17, 2007, now U.S. Pat. No. 8,414,927 which claims priority under 35 U.S.C. §119 of U.S. Application No. 60/856,662, filed Nov. 3, 2006. The disclosure of each of the foregoing references is hereby incorporated by reference in its entirety.

FIELD

The disclosure relates to cross-linked polymer particles, as well as related compositions and methods.

BACKGROUND

Agents, such as therapeutic agents, can be delivered systemically, for example, by injection through the vascular system or oral ingestion, or they can be applied directly to a site where treatment is desired. In some cases, particles are used to deliver a therapeutic agent to a target site. Additionally or alternatively, particles may be used to perform embolization procedures and/or to perform radiotherapy procedures.

SUMMARY

In one aspect, the invention features a particles that includes a material that includes a polymer backbone bonded to a chemical species via a reaction product of at least two different functionalities. One of the at least two different functionalities is an azido functionality, and the particle has a maximum dimension of at most 5,000 microns.

In another aspect, the invention features a particles that includes a material that includes a polymer backbone bonded to a chemical species via a reaction product of at least two different functionalities. One of the at least two different functionalities is an alkyne functionality, and the particle has a maximum dimension of at most 5,000 microns.

In a further aspect, the invention features a particle that includes a first polymer backbone, a second polymer backbone and a reaction product of an azido functionality and an alkyne functionality. The reaction product is covalently bonded to the first and second polymer backbones to cross-link the first and second polymer backbones, and the particle has a maximum dimension of at most 5,000 microns.

In an additional aspect, the invention features a delivery device that includes a delivery vessel configured to delivery a composition into a body lumen, a polymer that includes a polymer backbone and a first functionality covalently bonded to the first polymer backbone, and a chemical species comprising a second functionality. The polymer and the chemical species are in the delivery vessel, and the first and second functionalities are different. The first and second functionalities are capable of reacting to form a product that bonds the polymer and the chemical species.

In one aspect, the invention features a method that includes providing a polymer comprising a polymer backbone and a first functionality, and providing a chemical species comprising a second functionality different from the first functionality. The method also includes reacting the first and second functionalities to form a reaction product, to form a material comprising the polymer backbone bonded to the chemical species via the reaction product of the first and second functionalities. The material is in the shape of a particle having a maximum dimension of at most 5,000 microns.

In another aspect, the invention features a method that includes bonding a polymer and a chemical species in a body lumen to form a gel in the body lumen. The polymer comprises a backbone and a first functionality covalently bonded to the first backbone, and the chemical species comprises a second functionality. The polymer and the chemical species are bonded via a reaction product of the first and second functionalities.

In a further aspect, the invention features a composition that includes a carrier fluid and a plurality of particles in the carrier fluid. At least some of the plurality of particles have a maximum dimension of at most 5,000 microns and are formed of a material that includes a polymer backbone bonded to a chemical species via a reaction product of at least two different functionalities. One of the at least two different functionalities comprising an azido functionality.

In an additional aspect, the invention features a composition that includes a carrier fluid and a plurality of particles in the carrier fluid. At least some of the plurality of particles have a maximum dimension of at most 5,000 microns and are formed of a material that includes a polymer backbone bonded to a chemical species via a reaction product of at least two different functionalities. One of the at least two different functionalities comprising an alkyne functionality.

In one aspect, the invention features a composition that includes a carrier fluid and a plurality of particles in the carrier fluid. At least some of the plurality of particles have a maximum dimension of at most 5,000 microns and are formed of a material comprising a first polymer backbone cross-linked to a second polymer backbone via a reaction product of at least two different functionalities.

In another aspect, the invention features a composition that includes a carrier fluid and a plurality of particles in the carrier fluid. At least some of the plurality of particles have a maximum dimension of at most 5,000 microns and include a polymer backbone, a chemical species and a reaction product of an azido functionality and a second functionality. The reaction product is covalently bonded to the polymer backbone and the chemical species.

In a further aspect, the invention features a composition that includes a carrier fluid and a plurality of particles in the carrier fluid. At least some of the plurality of particles have a maximum dimension of at most 5,000 microns and include a polymer backbone, a chemical species and a reaction product of an alkyne functionality and a second functionality. The reaction product is covalently bonded to the polymer backbone and the chemical species.

In an additional aspect, the invention features a composition that includes a carrier fluid and a plurality of particles in the carrier fluid. At least some of the plurality of particles have a maximum dimension of at most 5,000 microns and include a first polymer backbone, a second polymer backbone and a reaction product of an azido functionality and an alkyne functionality. The reaction product is covalently bonded to the first and second polymer backbones to cross-link the first and second polymer backbones.

Embodiments can include one or more of the following advantages.

The crosslinks that stabilize the particle can be biodegradable. For example, the reaction product that cross-links polymer backbones can be biodegradable. This can be advantageous, for example, when it is desirable for the particle(s) to be absent from a body lumen after some desired time period (e.g., after the embolization is complete).

One or more constituents of the particle can covalently bond to one or more therapeutic agents. This can be advantageous, for example, when it is desirable to use the particle(s) to treat a disease (e.g., cancer, such as a cancerous tumor) using a therapeutic agent, alone or in combination with embolization. In some embodiments, one or more of the functionalities (e.g., azido functionalities, alkyne functionalities) can covalently bond to one or more therapeutic agents. Alternatively or in addition, the particle can include pores in which one or more therapeutic agents can be disposed.

The polymer backbones can be cross-linked at relatively low temperature and/or under relatively mild conditions (e.g., without formalization, without acetalization). This can, for example, allow for one or more therapeutic agents to be combined with the polymers prior to cross-linking.

Features and advantages are in the description, drawings, and claims.

BRIEF DESCRIPTION OF THE DRAWINGS

FIG. 6 is a side view of the proximal end portion of an embodiment of a device.

FIG. 7 is a side view of the distal end portion of the device of FIG. 6.

DETAILED DESCRIPTION

Figure 1A:
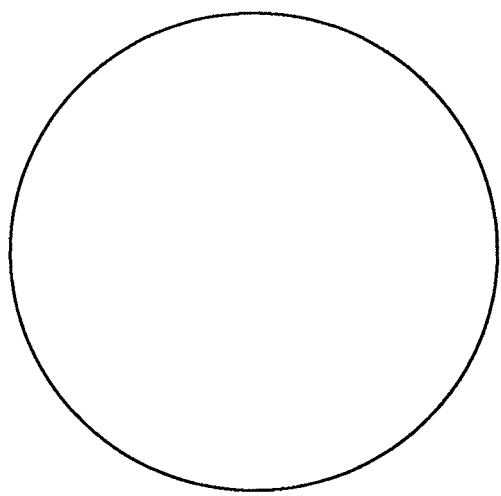
FIG. 1A is a side view of an embodiment of a particle.
Figure 1B:
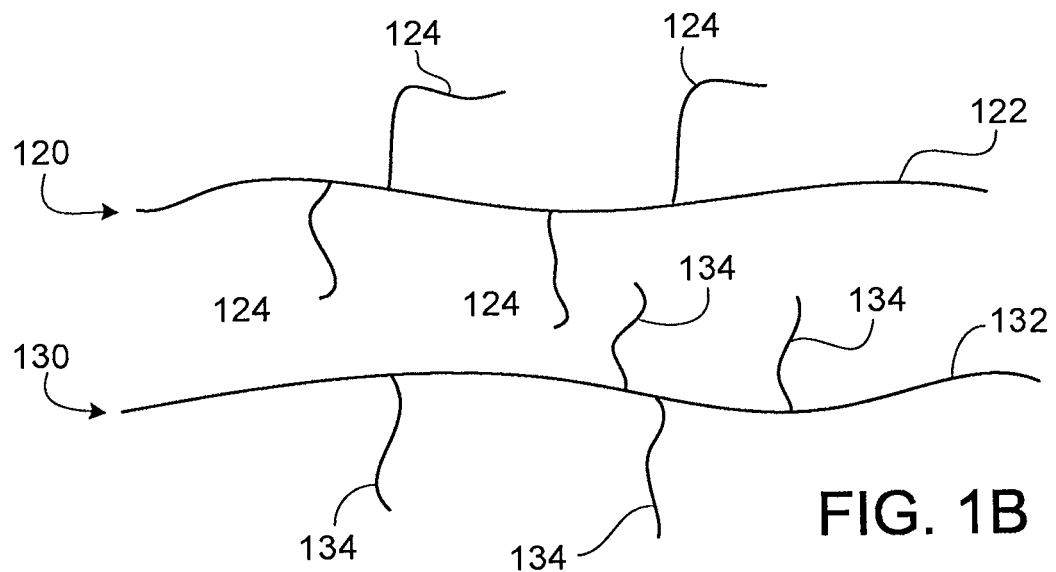
FIG. 1B depicts an embodiment of precursor materials to material from which the particle shown in FIG. 1A is formed.
Figure 1C:
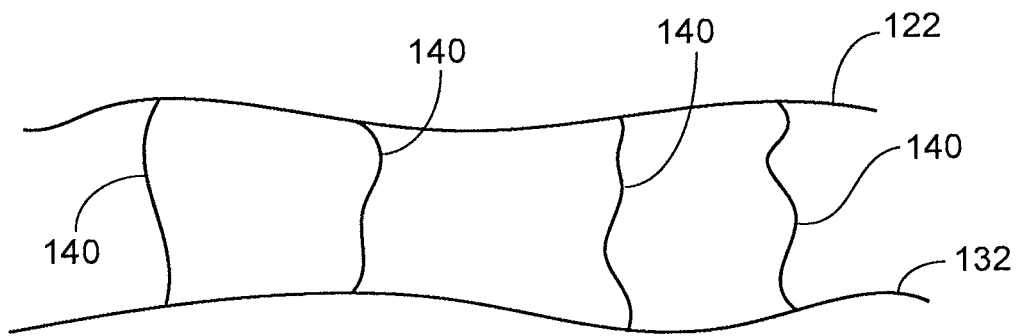
FIG. 1C depicts the material from which the particle shown in FIG. 1A is formed.

FIG. 1A shows a particle 100 that can be used, for example, in an embolization procedure. Particle 100 is formed of a material 110 that includes a first polymer backbone cross-linked to a second polymer backbone via a reaction product of at least two different functionalities. FIG. 1B depicts polymers 120 and 130 that are precursors to material 110. Polymer 120 includes a polymer backbone 122 and functionalities 124 covalently bonded to polymer backbone 122. Polymer 130 includes a polymer backbone 132 and functionalities 134 covalently bonded to polymer backbone 132. FIG. 1C depicts material 100 formed by the reaction of polymers 120 and 130. Material 110 includes polymer backbones 122 and 132 cross-linked by a reaction product 140 of functionalities 124 and 134.

In some embodiments, a polymer backbone can include multiple vinyl alcohol monomer units covalently bonded to each other. Such a polymer is referred to herein as a polyvinyl alcohol. As used herein, a vinyl alcohol monomer unit has the following structure:

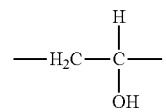

In certain embodiments, a polyvinyl alcohol can include monomer units other polyvinyl alcohol monomer units. For example, a polyvinyl alcohol can include polyvinyl formal monomer units and/or polyvinyl acetate monomer units. As referred to herein, a vinyl formal monomer unit has the following structure:

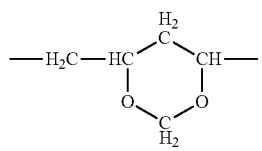

As referred to herein, a vinyl acetate monomer unit has the following structure:

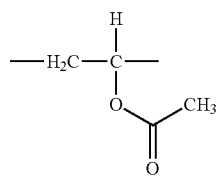

In some embodiments, a polyvinyl alcohol can have the formula that is schematically represented below, in which x, y and z each are integers. Generally, however, x is zero.

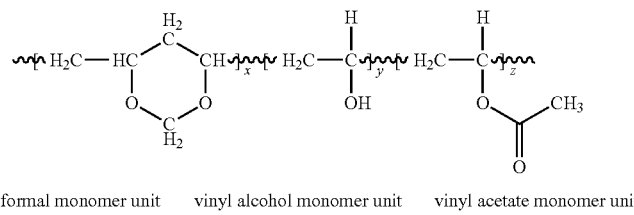

vinyl formal monomer unit   vinyl alcohol monomer unit   vinyl acetate monomer unit In some embodiments, a polyvinyl alcohol can include at least one percent by weight (e.g., at least five percent by weight, at least 10 percent by weight, at least 25 percent by weight, at least 50 percent by weight), and/or at most 95 percent by weight (e.g., at most 90 percent by weight, at most 80 percent by weight, at most 50 percent by weight, at most 20 percent by weight) vinyl alcohol monomer units. The percent by weight of a monomer unit in a polymer can be determined using standard techniques, such as, for example, IR, UV and/or NMR spectroscopies.

Generally, the polymer will contain little or no vinyl formal monomer units. In some embodiments, the polymer can include at most 10 percent by weight (e.g., at most 5 percent by weight, at most 2 percent by percent by weight) vinyl formal monomer units and/or at least 0.1 percent by weight (e.g., at least 0.5 percent by weight, at least 1 percent by weight) vinyl formal monomer units.

In some embodiments, a polyvinyl alcohol can include at least 0.5 percent by weight (e.g., at least one percent by weight, at least five percent by weight, at least 10 percent by weight), and/or at most 20 percent by weight (e.g., at most 15 percent by weight, at most 10 percent by weight, at most five percent by weight) vinyl acetate monomer units.

Alternatively or in addition, other polymers may be used as a polymer backbone. Examples of polymers include polyHEMAs, carbohydrates, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly(d-lactic-co-glycolic) acids) and copolymers or mixtures thereof. Polymers are described, for example, in Lanphere et al., U.S. Patent Application Publication No. US 2004/0096662 A1, published on May 20, 2004, and entitled "Embolization"; Song et al., U.S. patent application Ser. No. 11/314,056, filed on Dec. 21, 2005, and entitled "Block Copolymer Particles"; and Song et al., U.S. patent application Ser. No. 11/314,557, filed on Dec. 21, 2005, and entitled "Block Copolymer Particles", all of which are incorporated herein by reference.

While described above as being bonded to a polymer backbone, more generally, a functionality (e.g., an alkyne functionality, an azido functionality) can be bonded to any chemical species, such as, for example, a low molecular weight species or an oligomer. The chemical species can be biodegradable and/or render a particle biodegradable when incorporated therein. As used herein, biodegradable polymer is a polymer containing chemical linkages (e.g., vinyl alcohol monomer linkages) that can be broken down in the body by hydrolysis, enzymes and/or bacteria to form a lower molecular weight species that can dissolve and be excreted by the body.

In some embodiments, a functionality can be covalently bonded with a multifunctional (e.g., difunctional, trifunctional, etc.) oligomer. Optionally, the oligomers can be biodegradable. Examples of biodegradable oligomers include low molecular weight PLAs, PGAs, polycaprolactones (e.g., Poly-ε-caprolactone), polyglycolic acids, poly(lactic-co-glycolic) acids (e.g., poly(d-lactic-co-glycolic) acids, poly lactic acid (e.g., Poly-L-lactic acid, Poly-D,L-lactic acid), poly-p-dioxanons, tri-methylen carbonates, poly anhydrides, poly ortho esters, poly urethanes, poly amino acids, poly hydroxy alcanoates, poly phosphazenes, poly-b-malein acids, collagen (Proteins), chitin, chitosan (polysaccharides), fibrin and albumin. Optionally, the oligomers can be non-biodegradable. Examples of such oligomers include polyHEMAs, carbohydrates, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, and polymethylmethacrylates.

In certain embodiments, one or more additional functionalities can be included on the polymer backbone. The functionalities can be selected, for example influence one or more physical characteristics (e.g., compressability) and/or one or more chemical characteristics (e.g., therapeutic agent release rate) of the particle. Examples of such additional functionalities include amines (e, g., propargyl amine, 2-azidoethylamine), alcohols, carboxyl, long chain hydrocarbons, amides and aldehydes.

The product of the reaction of an azido functionality with an alkyne functionality is a 1,2,3-triazole group. Such groups have multiple tertiary nitrogen atoms. These nitrogen atoms can be used to form ionic complexes with certain therapeutic agents (e.g., acidic drugs), which can, for example, be used to modulate the release of therapeutic agent from a particle.

Reaction of functionalities 124 and 134 can be carried out using known methods. In some embodiments (e.g., when reacting an alkyne functionality with an azido functionality), the functionalities are reacted via a cycloaddition reaction, such as the Huisgen azide-alkyne [3+2] cycloaddition reaction. Exemplary conditions for such reactions are disclosed, for example, in Kolb, H. C. et al., *Drug Discovery Today* 2003, 8, 1128-1137; Speers, A. E. et al., *J. Am. Chem. Soc.* 2003, 125, 4686-4687; Yang Q. et al., *J. Am. Chem. Soc.* 2003, 125, 3192-3193; Rostovtsev V. V. et al., *J. Am. Chem. Soc.* 2002, 41, 2596-2599; Rostovtsev V. V. et al., *Angew. Chem., Int. Ed.* 2002, 41, 2596-2599.

The particles can be formed using any desired technique. As an example, particles can be formed by using a droplet generator to form a stream of drops of the polymers that serve as precursors to the material from which the particle will be formed, placing the stream of drops into a bath of an appropriate liquid (e.g., water, alcohol-water mixtures), and then homogenizing the liquid/polymer to form the drops. Exemplary droplet generator systems and methods are described below. Alternatively or additionally, particles can be formed using other techniques, such as, for example, molding and/or oil-water emulsions.

In general, the maximum dimension of particle 100 is 5,000 microns or less (e.g., from two microns to 5,000 microns; from 10 microns to 5,000 microns; from 40 microns to 2,000 microns; from 100 microns to 700 microns; from 500 microns to 700 microns; from 100 microns to 500 microns; from 100 microns to 300 microns; from 300 microns to 500 microns; from 500 microns to 1,200 microns; from 500 microns to 700 microns; from 700 microns to 900 microns; from 900 microns to 1,200 microns; from 1,000 microns to 1,200 microns). In some embodiments, the maximum dimension of particle 100 is 5,000 microns or less (e.g., 4,500 microns or less, 4,000 microns or less, 3,500 microns or less, 3,000 microns or less, 2,500 microns or less; 2,000 microns or less; 1,500 microns or less; 1,200 microns or less; 1,150 microns or less; 1,100 microns or less; 1,050 microns or less; 1,000 microns or less; 900 microns or less; 700 microns or less; 500 microns or less; 400 microns or less; 300 microns or less; 100 microns or less; 50 microns or less; 10 microns or less; five microns or less) and/or one micron or more (e.g., five microns or more; 10 microns or more; 50 microns or more; 100 microns or more; 300 microns or more; 400 microns or more; 500 microns or more; 700 microns or more; 900 microns or more; 1,000 microns or more; 1,050 microns or more; 1,100 microns or more; 1,150 microns or more; 1,200 microns or more; 1,500 microns or more; 2,000 microns or more; 2,500 microns or more). In some embodiments, the maximum dimension of particle 100 is less than 100 microns (e.g., less than 50 microns).

In some embodiments, particle 100 can be substantially spherical. In certain embodiments, particle 100 can have a sphericity of 0.8 or more (e.g., 0.85 or more, 0.9 or more, 0.95 or more, 0.97 or more). Particle 100 can be, for example, manually compressed, essentially flattened, while wet to 50 percent or less of its original diameter and then, upon exposure to fluid, regain a sphericity of 0.8 or more (e.g., 0.85 or more, 0.9 or more, 0.95 or more, 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where Da=√(4A/π); Dp=P/π; A=pixel area; P=pixel perimeter), is a value from zero to one, with one representing a perfect circle.

Figure 2A:
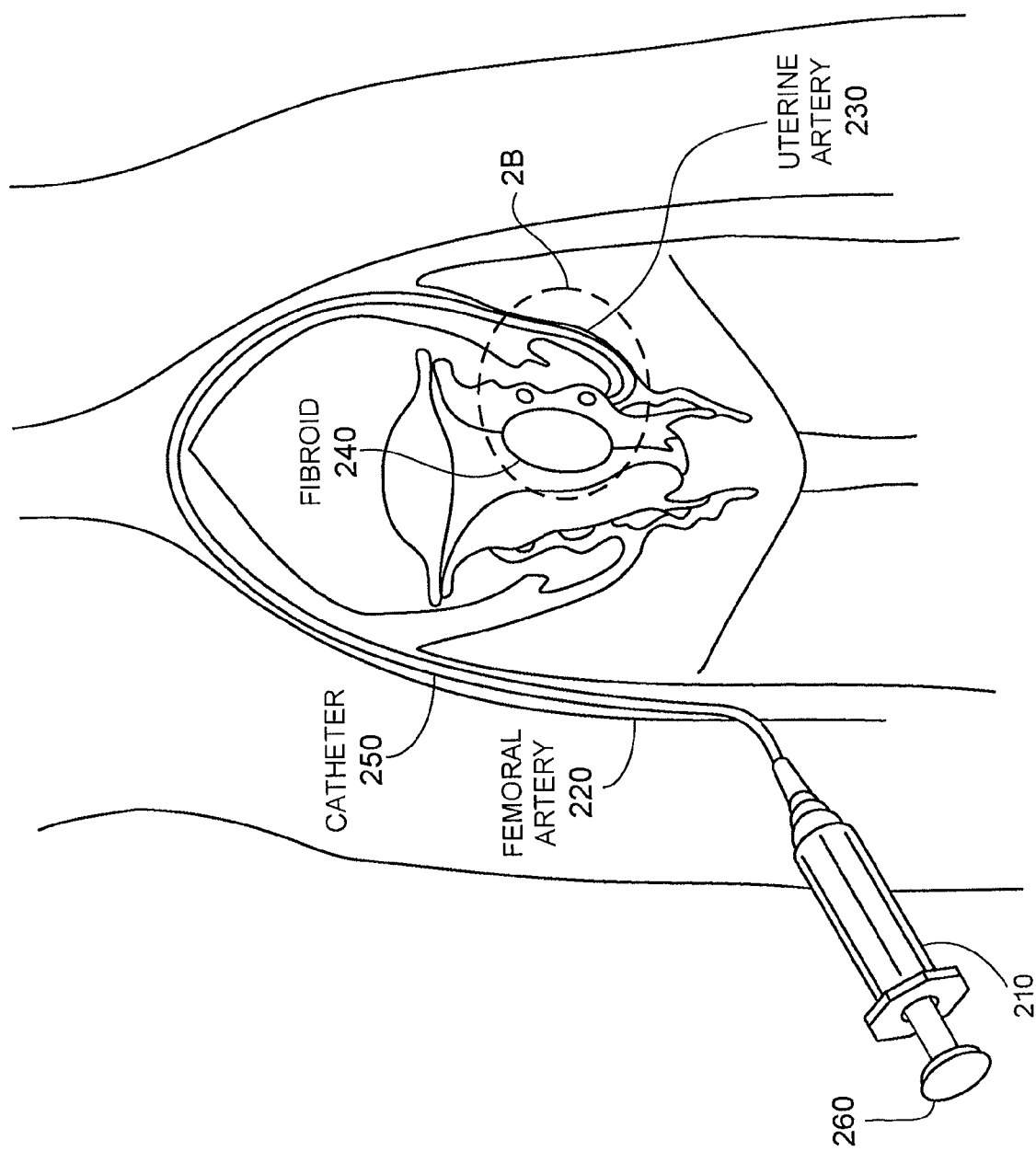
FIG. 2B is a greatly enlarged view of region 2B in FIG. 2A.
Figure 2B:
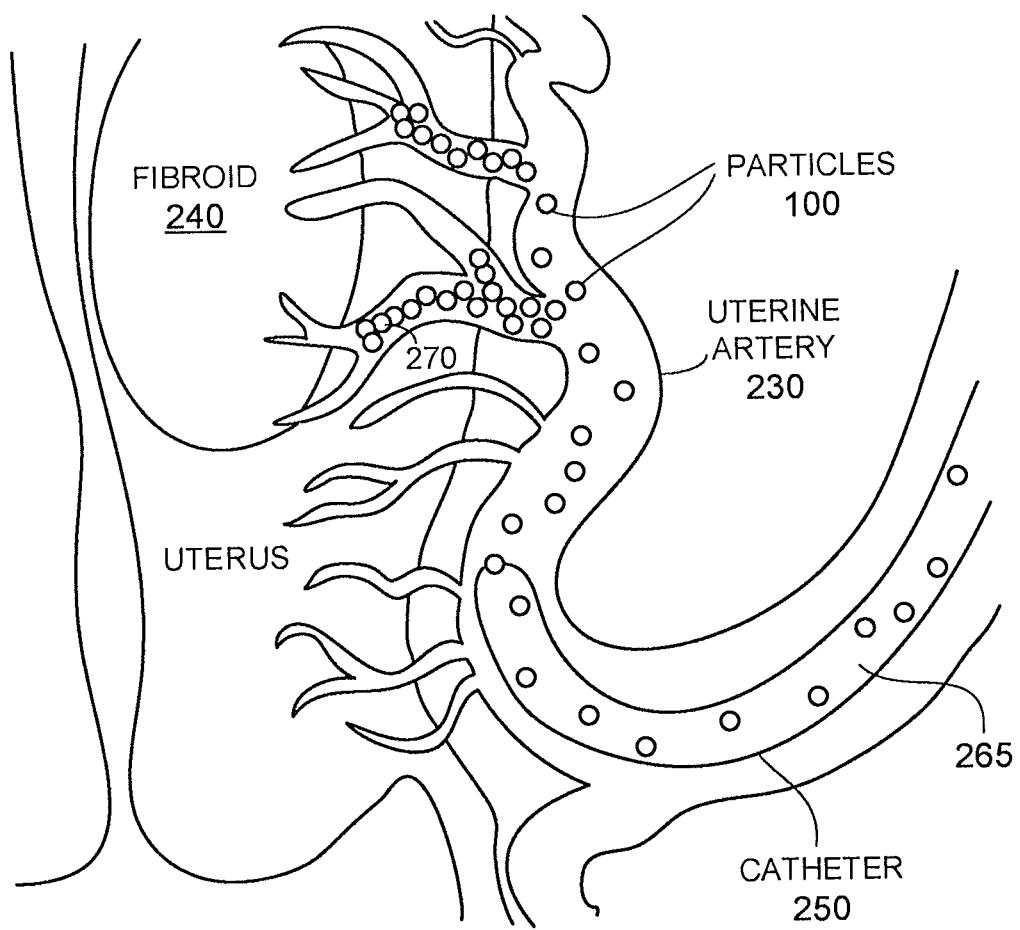

Multiple particles can be combined with a carrier fluid (e.g., a pharmaceutically acceptable carrier, such as a saline solution, a contrast agent, or both) to form a composition, which can then be delivered to a site and used to embolize the site. FIGS. 2A and 2B illustrate the use of a composition including particles to embolize a lumen of a subject. As shown, a composition including particles 100 and a carrier fluid is injected into a vessel through an instrument such as a catheter 250. Catheter 250 is connected to a syringe barrel 210 with a plunger 260. Catheter 250 is inserted, for example, into a femoral artery 220 of a subject. Catheter 250 delivers the composition to, for example, occlude a uterine artery 230 leading to a fibroid 240 located in the uterus of a female subject. The composition is initially loaded into syringe 210. Plunger 260 of syringe 210 is then compressed to deliver the composition through catheter 250 into a lumen 265 of uterine artery 230.

FIG. 2B, which is an enlarged view of section 2B of FIG. 2A, shows uterine artery 230, which is subdivided into smaller uterine vessels 270 (e.g., having a diameter of two millimeters or less) that feed fibroid 240. The particles 100 in the composition partially or totally fill the lumen of uterine artery 230, either partially or completely occluding the lumen of the uterine artery 230 that feeds uterine fibroid 240.

Compositions including particles such as particles 100 can be delivered to various sites in the body, including, for example, sites having cancerous lesions, such as the breast, prostate, lung, thyroid, or ovaries. The compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are, for example, abnormal collections of blood vessels (e.g. in the brain) which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of a composition can vary based on the nature, location and severity of the condition to be treated, as well as the route of administration. A physician treating the condition, disease or disorder can determine an effective amount of composition. An effective amount of embolic composition refers to the amount sufficient to result in amelioration of symptoms and/or a prolongation of survival of the subject, or the amount sufficient to prophylactically treat a subject. The compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

A composition can include a mixture of particles, or can include particles that are all of the same type. In some embodiments, a composition can be prepared with a calibrated concentration of particles for ease of delivery by a physician. A physician can select a composition of a particular concentration based on, for example, the type of procedure to be performed. In certain embodiments, a physician can use a composition with a relatively high concentration of particles during one part of an embolization procedure, and a composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from one minute to 20 minutes (e.g. from one minute to 10 minutes, from two minutes to seven minutes, from three minutes to six minutes).

In some embodiments, particles can be suspended in a physiological solution by matching the density of the solution to the density of the particles. In certain embodiments, the particles and/or the physiological solution can have a density of from one gram per cubic centimeter to 1.5 grams per cubic centimeter (e.g., from 1.2 grams per cubic centimeter to 1.4 grams per cubic centimeter, from 1.2 grams per cubic centimeter to 1.3 grams per cubic centimeter).

In certain embodiments, the carrier fluid of a composition can include a surfactant. The surfactant can help the particles to mix evenly in the carrier fluid and/or can decrease the likelihood of the occlusion of a delivery device (e.g., a catheter) by the particles. In certain embodiments, the surfactant can enhance delivery of the composition (e.g., by enhancing the wetting properties of the particles and facilitating the passage of the particles through a delivery device). In some embodiments, the surfactant can decrease the occurrence of air entrapment by the particles in a composition (e.g., by porous particles in a composition). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, a composition can include from 0.05 percent by weight to one percent by weight (e.g., 0.1 percent by weight, 0.5 percent by weight) of a surfactant. A surfactant can be added to the carrier fluid prior to mixing with the particles and/or can be added to the particles prior to mixing with the carrier fluid.

In some embodiments, among the particles delivered to a subject (e.g., in a composition), the majority (e.g., 50 percent or more, 60 percent or more, 70 percent or more, 80 percent or more, 90 percent or more) of the particles can have a maximum dimension of 5,000 microns or less (e.g., 4,500 microns or less; 4,000 microns or less; 3,500 microns or less; 3,000 microns or less; 2,500 microns or less; 2,000 microns or less; 1,500 microns or less; 1,200 microns or less; 1,150 microns or less; 1,100 microns or less; 1,050 microns or less; 1,000 microns or less; 900 microns or less; 700 microns or less; 500 microns or less; 400 microns or less; 300 microns or less; 100 microns or less; 50 microns or less; 10 microns or less; five microns or less) and/or one micron or more (e.g., five microns or more; 10 microns or more; 50 microns or more; 100 microns or more; 300 microns or more; 400 microns or more; 500 microns or more; 700 microns or more; 900 microns or more; 1,000 microns or more; 1,050 microns or more; 1,100 microns or more; 1,150 microns or more; 1,200 microns or more; 1,500 microns or more; 2,000 microns or more; 2,500 microns or more). In some embodiments, among the particles delivered to a subject, the majority of the particles can have a maximum dimension of less than 100 microns (e.g., less than 50 microns).

In certain embodiments, the particles delivered to a subject (e.g., in a composition) can have an arithmetic mean maximum dimension of 5,000 microns or less (e.g., 4,500 microns or less; 4,000 microns or less; 3,500 microns or less; 3,000 microns or less; 2,500 microns or less; 2,000 microns or less; 1,500 microns or less; 1,200 microns or less; 1,150 microns or less; 1,100 microns or less; 1,050 microns or less; 1,000 microns or less; 900 microns or less; 700 microns or less; 500 microns or less; 400 microns or less; 300 microns or less; 100 microns or less; 50 microns or less; 10 microns or less; five microns or less) and/or one micron or more (e.g., five microns or more; 10 microns or more; 50 microns or more; 100 microns or more; 300 microns or more; 400 microns or more; 500 microns or more; 700 microns or more; 900 microns or more; 1,000 microns or more; 1,050 microns or more; 1,100 microns or more; 1,150 microns or more; 1,200 microns or more; 1,500 microns or more; 2,000 microns or more; 2,500 microns or more). In some embodiments, the particles delivered to a subject can have an arithmetic mean maximum dimension of less than 100 microns (e.g., less than 50 microns).

Exemplary ranges for the arithmetic mean maximum dimension of particles delivered to a subject include from 100 microns to 500 microns; from 100 microns to 300 microns; from 300 microns to 500 microns; from 500 microns to 700 microns; from 700 microns to 900 microns; from 900 microns to 1,200 microns; and from 1,000 microns to 1,200 microns. In general, the particles delivered to a subject (e.g., in a composition) can have an arithmetic mean maximum dimension in approximately the middle of the range of the diameters of the individual particles, and a variance of 20 percent or less (e.g. 15 percent or less, 10 percent or less).

In some embodiments, the arithmetic mean maximum dimension of the particles delivered to a subject (e.g., in a composition) can vary depending upon the particular condition to be treated. As an example, in certain embodiments in which the particles are used to embolize a liver tumor, the particles delivered to the subject can have an arithmetic mean maximum dimension of 500 microns or less (e.g., from 100 microns to 300 microns; from 300 microns to 500 microns). As another example, in some embodiments in which the particles are used to embolize a uterine fibroid, the particles delivered to the subject can have an arithmetic mean maximum dimension of 1,200 microns or less (e.g., from 500 microns to 700 microns; from 700 microns to 900 microns; from 900 microns to 1,200 microns). As an additional example, in certain embodiments in which the particles are used to treat a neural condition (e.g., a brain tumor) and/or head trauma (e.g., bleeding in the head), the particles delivered to the subject can have an arithmetic mean maximum dimension of less than 100 microns (e.g., less than 50 microns). As a further example, in some embodiments in which the particles are used to treat a lung condition, the particles delivered to the subject can have an arithmetic mean maximum dimension of less than 100 microns (e.g., less than 50 microns). As another example, in certain embodiments in which the particles are used to treat thyroid cancer, the particles can have an arithmetic maximum dimension of 1,200 microns or less (e.g., from 1,000 microns to 1,200 microns). As an additional example, in some embodiments in which the particles are used only for therapeutic agent delivery, the particles can have an arithmetic mean maximum dimension of less than 100 microns (e.g., less than 50 microns, less than 10 microns, less than five microns).

The arithmetic mean maximum dimension of a group of particles can be determined using a Beckman Coulter Rapid-VUE Image Analyzer version 2.06 (Beckman Coulter, Miami, Fla.), described above. The arithmetic mean maximum dimension of a group of particles (e.g., in a composition) can be determined by dividing the sum of the diameters of all of the particles in the group by the number of particles in the group.

In some embodiments, particle 100 can have pores. For example, the polymer can form a matrix in which the pores are present. Additionally or alternatively, particle 100 can have one or more cavities. For example, particle 100 can be formed so that the polymer surrounds one or more cavities.

A pore has a maximum dimension of at least 0.01 micron (e.g., at least 0.05 micron, at least 0.1 micron, at least 0.5 micron, at least one micron, at least five microns, at least 10 microns, at least 15 microns, at least 20 microns, at least 25 microns, at least 30 microns, at least 35 microns, at least 50 microns, at least 100 microns, at least 150 microns, at least 200 microns, at least 250 microns), and/or at most 300 microns (e.g., at most 250 microns, at most 200 microns, at most 150 microns, at most 100 microns, at most 50 microns, at most 35 microns, at most 30 microns, at most 25 microns, at most 20 microns, at most 15 microns, at most 10 microns, at most five microns, at most one micron, at most 0.5 micron, at most 0.1 micron, at most 0.05 micron).

A cavity has a maximum dimension of at least one micron (e.g., a least five microns, at least 10 microns, at least 25 microns, at least 50 microns, at least 100 microns, at least 250 microns, at least 500 microns, at least 750 microns) and/or at most 1,000 microns (e.g., at most 750 microns, at most 500 microns, at most 250 microns, at most 100 microns, at most 50 microns, at most 25 microns, at most 10 microns, at most five microns).

The presence of one or more cavities and/or one or more pores can enhance the ability of particle 100 to retain and/or deliver a relatively large volume of therapeutic agent. As an example, in some embodiments, a cavity can be used to store a relatively large volume of therapeutic agent, and/or pores can be used to deliver the relatively large volume of therapeutic agent into a target site within a body of a subject at a controlled rate. As another example, in certain embodiments, both a cavity and pores can be used to store and/or deliver one or more therapeutic agents. In some embodiments, a cavity can contain one type of therapeutic agent, while pores can contain a different type of therapeutic agent. As described above, particle 100 can be used to deliver one or more therapeutic agents (e.g., a combination of therapeutic agents) to a target site. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Examples of radioactive species include yttrium ($^{90}$Y), holmium ($^{166}$Ho), phosphorus ($^{32}$P), ($^{177}$Lu), actinium ($^{225}$Ac), praseodymium, astatine ($^{211}$At) rhenium ($^{186}$Re), bismuth ($^{212}$Bi or $^{213}$Bi), samarium ($^{153}$Sm), iridium ($^{192}$Ir), rhodium ($^{105}$Rh), iodine ($^{131}$I or $^{125}$I), indium ($^{111}$In), technetium ($^{99}$Tc), phosphorus ($^{32}$P), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), and/or gallium ($^{67}$Ga). In some embodiments, yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), holmium ($^{166}$Ho), samarium ($^{153}$Sm), iridium ($^{192}$Ir), and/or rhodium ($^{105}$Rh) can be used as therapeutic agents. In certain embodiments, yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), holmium ($^{166}$Ho), samarium ($^{153}$Sm), iridium ($^{192}$Ir), rhodium ($^{105}$Rh), iodine ($^{131}$I or $^{125}$I), indium ($^{111}$In), technetium ($^{99}$Tc), phosphorus ($^{32}$P), carbon ($^{14}$C), and/or tritium ($^{3}$H) can be used as a radioactive label (e.g., for use in diagnostics). In some embodiments, a radioactive species can be a radioactive molecule that includes antibodies containing one or more radioisotopes, for example, a radiolabeled antibody. Radioisotopes that can be bound to antibodies include, for example, iodine ($^{131}$I or $^{125}$I), yttrium ($^{90}$Y), lutetium ($^{177}$Lu), actinium ($^{225}$Ac), praseodymium, astatine ($^{211}$At), rhenium ($^{105}$Rh), bismuth ($^{212}$Bi or $^{213}$Bi), indium ($^{111}$In), technetium ($^{99}$Tc), phosphorus ($^{32}$P), rhodium ($^{105}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), and/or gallium ($^{67}$Ga). Examples of antibodies include monoclonal and polyclonal antibodies including RS7, Mov18, MN-14 IgG, CC49, COL-1, mAB A33, NP-4 F(ab')2 anti-CEA, anti-PSMA, ChL6, m-170, or antibodies to CD20, CD74 or CD52 antigens. Examples of radioisotope/antibody pairs include m-170 MAB with $^{90}$Y. Examples of commercially available radioisotope/antibody pairs include Zevalin™ (IDEC pharmaceuticals, San Diego, Calif.) and Bexxar™ (Corixa corporation, Seattle, Wash.). Further examples of radioisotope/antibody pairs can be found in *J. Nucl. Med.* 2003, April: 44(4): 632-40.

Non-limiting examples of therapeutic agents include anti-thrombogenic agents; thrombogenic agents; agents that promote clotting; agents that inhibit clotting; antioxidants; angiogenic and anti-angiogenic agents and factors; anti-proliferative agents (e.g., agents capable of blocking smooth muscle cell proliferation, such as rapamycin); calcium entry blockers (e.g., verapamil, diltiazem, nifedipine); targeting factors (e.g., polysaccharides, carbohydrates); agents that can stick to the vasculature (e.g., charged moieties, such as gelatin, chitosan, and collagen); and survival genes which protect against cell death (e.g., anti-apoptotic Bcl-2 family factors and Akt kinase).

Examples of non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, antiplatelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Examples of genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents are disclosed in Kunz et al., U.S. Pat. No. 5,733,925, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

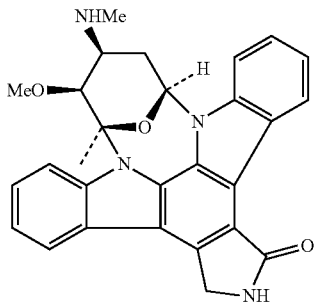 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

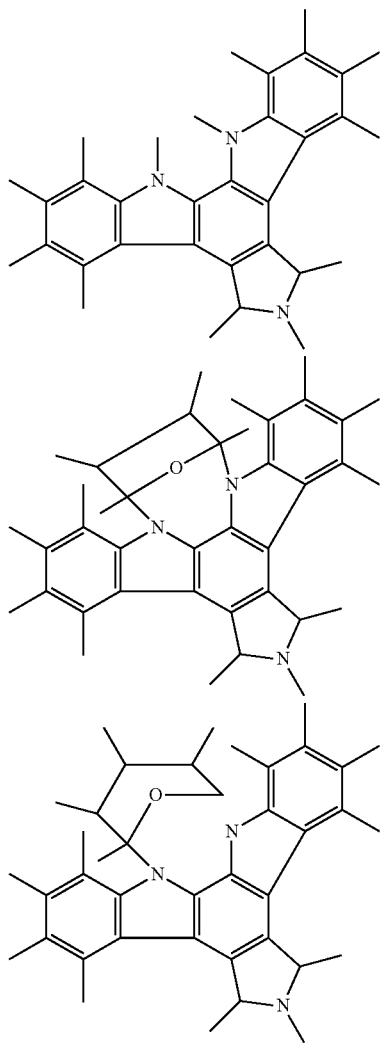

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP Iib/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), Fxa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, antisense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

In some embodiments, a therapeutic agent can be hydrophilic. An example of a hydrophilic therapeutic agent is doxorubicin hydrochloride. In certain embodiments, a therapeutic agent can be hydrophobic. Examples of hydrophobic therapeutic agents include paclitaxel, cisplatin, tamoxifen, and doxorubicin base. In some embodiments, a therapeutic agent can be lipophilic. Examples of lipophilic therapeutic agents include taxane derivatives (e.g., paclitaxel) and steroidal materials (e.g., dexamethasone).

Therapeutic agents are described, for example, in DiMatteo et al., U.S. Patent Application Publication No. US 2004/0076582 A1, published on Apr. 22, 2004, and entitled "Agent Delivery Particle"; Schwarz et al., U.S. Pat. No. 6,368,658; Buiser et al., U.S. patent application Ser. No. 11/311,617, filed on Dec. 19, 2005, and entitled "Coils"; and Song, U.S. patent application Ser. No. 11/355,301, filed on Feb. 15, 2006, and entitled "Block Copolymer Particles", all of which are incorporated herein by reference. In certain embodiments, in addition to or as an alternative to including therapeutic agents, particle 100 can include one or more radiopaque materials, materials that are visible by magnetic resonance imaging (MRI-visible materials), ferromagnetic materials, and/or contrast agents (e.g., ultrasound contrast agents). Radiopaque materials, MRI-visible materials, ferromagnetic materials, and contrast agents are described, for example, in Rioux et al., U.S. Patent Application Publication No. US 2004/0101564 A1, published on May 27, 2004, and entitled "Embolization", which is incorporated herein by reference.

Figure 3:
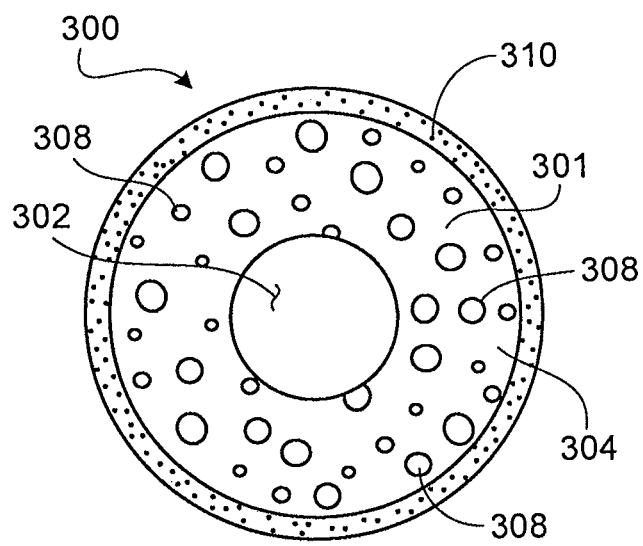
FIG. 3 is a cross-sectional view of an embodiment of a particle.

In certain embodiments, a particle can also include a coating. For example, FIG. 3 shows a particle 300 having an interior region 301 including a cavity 302 surrounded by a matrix 304. Matrix 304 includes pores 308, and is formed of material 110 described above. Particle 300 additionally includes a coating 310 formed of a polymer (e.g., alginate) that is different from the polymer in matrix 304. Coating 310 can, for example, regulate the release of therapeutic agent from particle 300, and/or provide protection to interior region 301 of particle 300 (e.g., during delivery of particle 300 to a target site). In certain embodiments, coating 310 can be formed of a bioerodible and/or bioabsorbable material that can erode and/or be absorbed as particle 300 is delivered to a target site. This can, for example, allow interior region 301 to deliver a therapeutic agent to the target site once particle 300 has reached the target site. A bioerodible material can be, for example, a polysaccharide (e.g., alginate); a polysaccharide derivative; an inorganic, ionic salt; a water soluble polymer (e.g., polyvinyl alcohol, such as polyvinyl alcohol that has not been cross-linked); biodegradable poly DL-lactide-poly ethylene glycol (PELA); a hydrogel (e.g., polyacrylic acid, hyaluronic acid, gelatin, carboxymethyl cellulose); a polyethylene glycol (PEG); chitosan; a polyester (e.g., a polycaprolactone); a poly(ortho ester); a polyanhydride; a poly(lactic-co-glycolic) acid (e.g., a poly(d-lactic-co-glycolic) acid); a poly(lactic acid) (PLA); a poly(glycolic acid) (PGA); or a combination thereof. In some embodiments, coating 310 can be formed of a swellable material, such as a hydrogel (e.g., polyacrylamide co-acrylic acid). The swellable material can be made to swell by, for example, changes in pH, temperature, and/or salt. In certain embodiments in which particle 300 is used in an embolization procedure, coating 310 can swell at a target site, thereby enhancing occlusion of the target site by particle 300.

Figure 4:
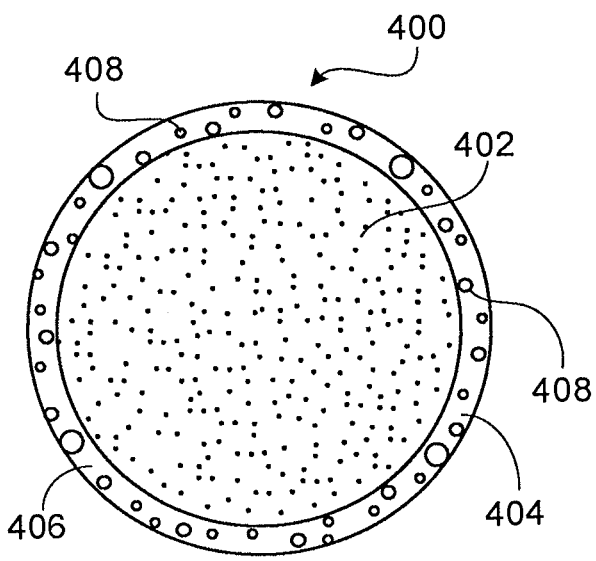
FIG. 4 is a cross-sectional view of an embodiment of a particle.

In some embodiments, a particle can include a porous coating that is formed of material 110 described above. For example, FIG. 4 shows a particle 400 including an interior region 402 and a coating 404. Coating 404 is formed of a matrix 406 that is formed of material 110 described above. Coating 404 also includes pores 408. In certain embodiments, interior region 402 can be formed of a swellable material. Pores 408 in coating 404 can expose interior region 402 to changes in, for example, pH, temperature, and/or salt. When interior region 402 is exposed to these changes, the swellable material in interior region 402 can swell, thereby causing particle 400 to become enlarged. In certain embodiments, coating 404 can be relatively flexible, and can accommodate the swelling of interior region 402. The enlargement of particle 400 can, for example, enhance occlusion during an embolization procedure.

Examples of swellable materials include hydrogels, such as polyacrylic acid, polyacrylamide co-acrylic acid, hyaluronic acid, gelatin, carboxymethyl cellulose, poly(ethylene oxide)-based polyurethane, polyaspartahydrazide, ethyleneglycoldiglycidylether (EGDGE), and polyvinyl alcohol (PVA) hydrogels. In some embodiments in which a particle includes a hydrogel, the hydrogel can be crosslinked, such that it may not dissolve when it swells. In other embodiments, the hydrogel may not be crosslinked, such that the hydrogel may dissolve when it swells.

In certain embodiments, a particle can include a coating that includes one or more therapeutic agents (e.g., a relatively high concentration of one or more therapeutic agents). One or more of the therapeutic agents can also be loaded into the interior region of the particle. Thus, the surface of the particle can release an initial dosage of therapeutic agent, after which the interior region of the particle can provide a burst release of therapeutic agent. The therapeutic agent on the surface of the particle can be the same as or different from the therapeutic agent in the interior region of the particle. The therapeutic agent on the surface of the particle can be applied to the particle by, for example, exposing the particle to a high concentration solution of the therapeutic agent.

In some embodiments, a therapeutic agent coated particle can include another coating over the surface of the therapeutic agent (e.g., a bioerodible polymer which erodes when the particle is administered). The coating can assist in controlling the rate at which therapeutic agent is released from the particle. For example, the coating can be in the form of a porous membrane. The coating can delay an initial burst of therapeutic agent release. In certain embodiments, the coating can be applied by dipping and/or spraying the particle. The bioerodible polymer can be a polysaccharide (e.g., alginate). In some embodiments, the coating can be an inorganic, ionic salt. Other examples of bioerodible coating materials include polysaccharide derivatives, water-soluble polymers (such as polyvinyl alcohol, e.g., that has not been cross-linked), biodegradable poly DL-lactide-poly ethylene glycol (PELA), hydrogels (e.g., polyacrylic acid, hyaluronic acid, gelatin, carboxymethyl cellulose), polyethylene glycols (PEG), chitosan, polyesters (e.g., polycaprolactones), poly(ortho esters), polyanhydrides, poly(lactic acids) (PLA), polyglycolic acids (PGA), poly(lactic-co-glycolic) acids (e.g., poly (d-lactic-co-glycolic) acids), and combinations thereof. The coating can include therapeutic agent or can be substantially free of therapeutic agent. The therapeutic agent in the coating can be the same as or different from an agent on a surface layer of the particle and/or within the particle. A polymer coating (e.g., a bioerodible coating) can be applied to the particle surface in embodiments in which a high concentration of therapeutic agent has not been applied to the particle surface. Coatings are described, for example, in DiMatteo et al., U.S. Patent Application Publication No. US 2004/0076582 A1, published on Apr. 22, 2004, and entitled "Agent Delivery Particle", which is incorporated herein by reference.

Figure 5A:
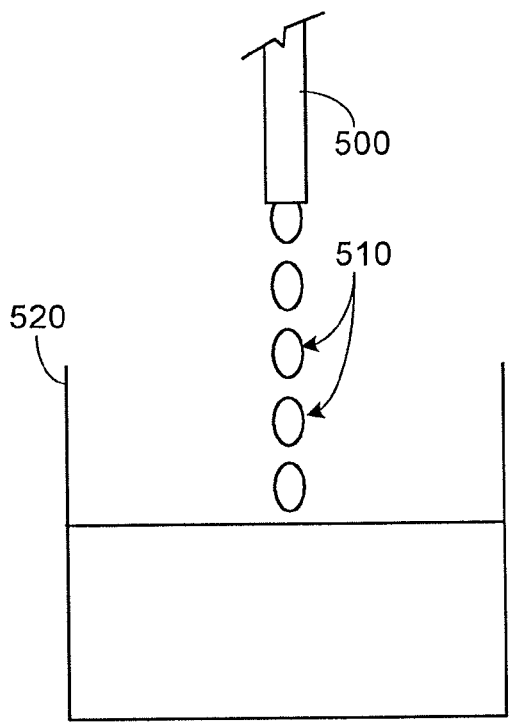
FIGS. 5A-5C are an illustration of an embodiment of a system and method for producing particles.
Figure 5B:
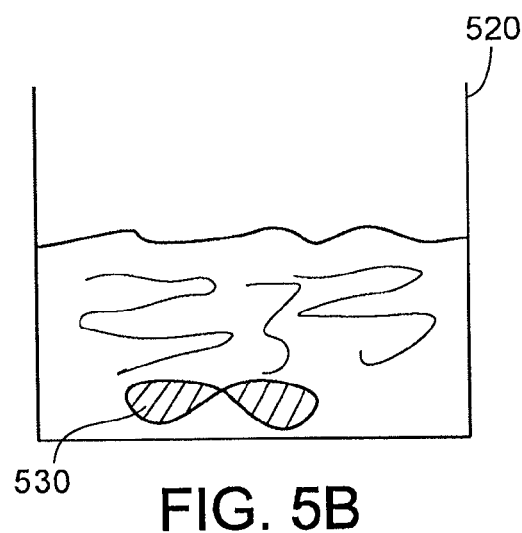
Figure 5C:
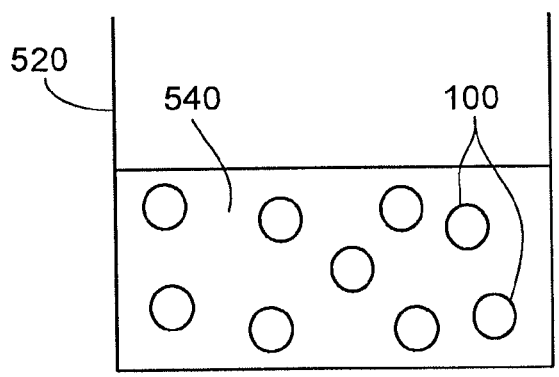

As an example, FIGS. 5A-5C show a single-emulsion process that can be used, for example, to make a particle. As shown in FIGS. 5A-5C, a drop generator 500 (e.g., a pipette, a needle) forms drops 510 of an organic solution including an organic solvent, a therapeutic agent, and polymers 120 and 130. Examples of organic solvents include glacial acetic acid, N,N-dimethylformamide (DMF), tetrahydrofuran (THF), and dimethylsulfoxide (DMSO). In certain embodiments, the organic solvent can be an aprotic polar solvent (e.g., DMF), which can dissolve both polar therapeutic agents and some non-polar therapeutic agents. In some embodiments, the organic solution can include at least five weight percent and/or at most 100 weight percent of the organic solvent. In general, as the concentration of the polymer in the organic solution increases, the sizes and/or masses of the particles that are formed from the organic solution can also increase. Typically, as the volume of organic solvent in the organic solution that is used to form drops 510 decreases, the rate at which particles form can increase. Generally, the rate of particle formation can increase as the volume of organic solvent that is used decreases. Without wishing to be bound by theory, it is believed that this occurs because the organic solvent can evaporate from drops 510 more quickly during the particle formation process. In this process, the azido and alkyne functionalities and can start reacting in the stream and the reaction of these functionalities can be completed in the vessel.

After they are formed, drops 510 fall from drop generator 500 into a vessel 520 that contains an aqueous solution including water (e.g., from 50 milliliters to 100 milliliters of water) and a surfactant. Examples of surfactants include lauryl sulfate, polyvinyl alcohols, poly(vinyl pyrrolidone) (PVP), and polysorbates (e.g., Tween® 20, Tween® 80). The concentration of the surfactant in the aqueous solution can be at least 0.1 percent w/v, and/or at most 20 percent w/v. For example, in some embodiments, the solution can include one percent w/v lauryl sulfate. Generally, as the concentration of the surfactant in the aqueous solution increases, the sphericity of the particles that are produced from the drop generation process, and the rate of formation of the particles during the particle formation process, can also increase. In some embodiments, the aqueous solution can be at a temperature of at least freezing temperature and/or at most 100° C. Typically, as the temperature of the aqueous solution increases, the rate at which particles (e.g., relatively rigid particles) form can also increase.

As FIG. 5B shows, after drops 510 have fallen into vessel 520, the solution is mixed (e.g., homogenized) using a stirrer 530. In some embodiments, the solution can be mixed for a period of at least one minute and/or at most 24 hours. In certain embodiments, mixing can occur at a temperature of at least freezing temperature and/or at most 100° C. The mixing results in a suspension 540 including particles 100 suspended in the solvent (FIG. 5C).

After particles 100 have been formed, they are separated from the solvent by, for example, filtration (e.g., through a drop funnel, filter paper, and/or a wire mesh), centrifuging followed by removal of the supernatant, and/or decanting. Thereafter, particles 100 are dried (e.g., by evaporation, by vacuum drying, by air drying).

While certain embodiments have been described, other embodiments are possible.

As an example, in some embodiments, enzymes and/or other bioactive agents can be mixed with the particles and/or co-injected with the particles (e.g. to facilitate degradation).

As another example, in some embodiments, particles can be used for tissue bulking. As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in Bourne et al., U.S. Patent Application Publication No. US 2003/0233150 A1, published on Dec. 18, 2003, and entitled "Tissue Treatment", which is incorporated herein by reference.

As an additional example, in certain embodiments, particles can be used to treat trauma and/or to fill wounds. In some embodiments, the particles can include one or more bactericidal agents and/or bacteriostatic agents.

As a further example, while compositions including particles suspended in at least one carrier fluid have been described, in certain embodiments, particles may not be suspended in any carrier fluid. For example, particles alone can be contained within a syringe, and can be injected from the syringe into tissue during a tissue ablation procedure and/or a tissue bulking procedure.

As an additional example, in some embodiments, particles having different shapes, sizes, physical properties, and/or chemical properties can be used together in a procedure (e.g., an embolization procedure). The different particles can be delivered into the body of a subject in a predetermined sequence or simultaneously. In certain embodiments, mixtures of different particles can be delivered using a multi-lumen catheter and/or syringe. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in Bell et al., U.S. Patent Application Publication No. US 2004/0091543 A1, published on May 13, 2004, and entitled "Embolic Compositions", and in DiCarlo et al., U.S. Patent Application Publication No. US 2005/0095428 A1, published on May 5, 2005, and entitled "Embolic Compositions", both of which are incorporated herein by reference.

As a further example, in some embodiments in which a particle including a polymer is used for embolization, the particle can also include (e.g., encapsulate) one or more embolic agents, such as a sclerosing agent (e.g., ethanol), a liquid embolic agent (e.g., n-butyl-cyanoacrylate), and/or a fibrin agent. The other embolic agent(s) can enhance the restriction of blood flow at a target site.

As another example, while particles including a polymer have been described, in some embodiments, other types of medical devices and/or therapeutic agent delivery devices can include such a polymer. For example, in some embodiments, a coil can include a polymer as described above. In certain embodiments, the coil can be formed by flowing a stream of the polymer into an aqueous solution, and stopping the flow of the polymer stream once a coil of the desired length has been formed. Coils are described, for example, in Elliott et al., U.S. patent application Ser. No. 11/000,741, filed on Dec. 1, 2004, and entitled "Embolic Coils", and in Buiser et al., U.S. patent application Ser. No. 11/311,617, filed on Dec. 19, 2005, and entitled "Coils", both of which are incorporated herein by reference. In certain embodiments, sponges (e.g., for use as a hemostatic agent and/or in reducing trauma) can include a polymer as described above. In some embodiments, coils and/or sponges can be used as bulking agents and/or tissue support agents in reconstructive surgeries (e.g., to treat trauma and/or congenital defects).

As a further example, in some embodiments, a treatment site can be occluded by using particles in conjunction with other occlusive devices. For example, particles can be used in conjunction with coils. Coils are described, for example, in Elliott et al., U.S. patent application Ser. No. 11/000,741, filed on Dec. 1, 2004, and entitled "Embolic Coils", and in Buiser et al., U.S. patent application Ser. No. 11/311,617, filed on Dec. 19, 2005, and entitled "Coils", both of which are incorporated herein by reference. In certain embodiments, particles can be used in conjunction with one or more gels.

Gels are described, for example, in Richard et al., U.S. Patent Application Publication No. US 2006/0045900 A1, published on Mar. 2, 2006, and entitled "Embolization", which is incorporated herein by reference. Additional examples of materials that can be used in conjunction with particles to treat a target site in a body of a subject include gel foams, glues, oils, and alcohol. Alternatively, or additionally, rather than using particles, a gel may be used. For example, as shown in FIGS. 6 and 7, a delivery device 1000 including a double-barrel syringe 2000 and a cannula 4000 that are capable of being coupled such that substances contained within syringe 2000 are introduced into cannula 4000. Syringe 2000 includes a first barrel 2200 having a tip 2300 with a discharge opening 2700, and a second barrel 2400 having a tip 2500 with a discharge opening 2900. Syringe 2000 further includes a first plunger 2600 that is movable in first barrel 2200, and a second plunger 2800 that is movable in second barrel 2400. As an example, first barrel 2200 can contain polymer 120, and second barrel 2400 can contain polymer 130. In its proximal end portion, cannula 4000 includes an adapter 4200 with a first branch 4400 that can connect with tip 2300, and a second branch 4600 that can connect with tip 2500. First branch 4400 is integral with a first tubular portion 5000 of cannula 4000, and second branch 4600 is integral with a second tubular portion 5200 of cannula 4000. First tubular portion 5000 is disposed within second tubular portion 5200. Delivery devices are described, for example, in Sahatjian et al., U.S. Pat. No. 6,629,947, which is incorporated herein by reference. When cannula 4000 is connected to syringe 2000 and plungers 2600 and 2800 are depressed, polymer 130 moves from second barrel 2400 into second tubular portion 5200, and polymer 120 moves from first barrel 2200 into first tubular portion 5000. Polymer 120 exits first tubular portion 5000 and contacts polymer 130 in a mixing section 6000 of second tubular portion 5200. Functionalities 124 and 134 react to form material 110 in the form of a gel (e.g., a biocompatible gel) 8000 within mixing section 6000. Gel 8000 exits delivery device 1000 at a distal end 5800 of mixing section 6000, and is delivered into a lumen 8500 of a vessel 9000 of a subject (e.g., an artery of a human) where gel 8000 can embolize lumen 8500 and/or deliver a therapeutic agent. In certain embodiments, gel 8000 is formed in lumen 8500 (e.g., when mixing section 6000 is in lumen 8500 when functionalities 124 and 134 react). In some embodiments, gel 8000 can be formed outside the body and subsequently delivered into lumen 8500.

Other embodiments are in the claims.

The invention claimed is:

1. A particle, comprising:
   a material comprising a first polymer backbone bonded to an anti-proliferative therapeutic agent via a 1,2,3-triazole group, wherein said anti-proliferative therapeutic agent further comprises a second polymer backbone selected from the group consisting of polyvinyl alcohol and polyglycolic acid, said anti-proliferative therapeutic agent selected from the group consisting of paclitaxel, 5-fluorouracil, cisplatin, methotrexate, doxorubicin, vinblastine, vincristine, epothilones, endostatin, angiostatin and angiopeptin.

2. A particle, comprising:
   a material comprising a polymer backbone bonded to an anti-proliferative therapeutic agent via a 1,2,3-triazole group, said anti-proliferative therapeutic agent selected from the group consisting of paclitaxel, 5-fluorouracil, cisplatin, methotrexate, doxorubicin, vinblastine, vincristine, epothilones, endostatin, angiostatin and angiopeptin, wherein said polymer backbone is selected from the group consisting of polyvinyl alcohol and polyglycolic acid.

3. A method of treating a disease, comprising:
   administering the particle of claim 1 to a subject under conditions such that an effective amount of said therapeutic agent is delivered to a site within said subject.

4. The method of claim 3, wherein said site is cancerous lesion.

5. The method of claim 4, wherein said cancerous lesion is selected from the group consisting of breast cancer, prostate cancer, lung cancer, thyroid cancer and ovarian cancer.

6. The method of claim 4, wherein said effective amount of said therapeutic agent reduces at least one symptom of said cancerous lesion.

7. The method of claim 3, wherein said particle is administered to said subject intravenously, subcutaneously, percutaneously, intratrachealy, intramuscularly, intramucosaly, intracutaneously, intra-articularly, orally or parenterally.

* * * * *